United States Patent [19]
Takahashi et al.

[11] Patent Number: 4,659,833
[45] Date of Patent: * Apr. 21, 1987

[54] OPTICALLY ACTIVE ISOCARBOSTYRIL DERIVATIVES AND A METHOD OF PREPARING THE SAME

[75] Inventors: Toshihiro Takahashi; Noriyoshi Sueda; Masahiro Tsuji, all of Kawagoe; Yoshiyuki Tahara, Tsurugashima; Hiroyasu Koyama, Ageo; Yoshikuni Suzuki, Ohmiya; Masao Nagase, Kawagoe; Toshiji Sugai, Fukuoka, all of Japan

[73] Assignee: Nisshin Flour Milling Co., Ltd., Tokyo, Japan

[*] Notice: The portion of the term of this patent subsequent to Jul. 2, 2002 has been disclaimed.

[21] Appl. No.: 731,963

[22] Filed: May 8, 1985

Related U.S. Application Data

[63] Continuation-in-part of Ser. No. 562,237, Dec. 16, 1983, Pat. No. 4,526,893.

[30] Foreign Application Priority Data

May 8, 1984 [JP] Japan .................................. 59-90173

[51] Int. Cl.$^4$ ........................................... C07D 217/24
[52] U.S. Cl. .................................. 546/142; 548/473; 564/347
[58] Field of Search ........................................ 546/142

[56] References Cited
PUBLICATIONS

"Chemical Abstracts", vol. 102, 1985, col. 102(9):78743p.

Primary Examiner—Glennon H. Hollrah
Assistant Examiner—James H. Turnipseed
Attorney, Agent, or Firm—Abelman, Frayne, Rezac & Schwab

[57] ABSTRACT

Four different optical isomers of a new compound, 1-[2'-(o-methoxyphenoxy)-1'-methylethylamino]-3-(4''-isocarbostyriloxy)-2-propanol are now provided as new substances. These four optical isomers are now named as (2R, 1'S)-1-[2'-(o-methoxyphenoxy)-1'-methylethylamino]-3-(4''-isocarbostyriloxy)-2-propanol, (2S, 1'S)-1-[2'-(o-methoxyphenoxy)-1'-methylethylamino]-3-(4''-isocarbostyriloxy)-2-propanol, (2S, 1'R)-1-[2'-(o-methoxyphenoxy)-1'-methylethylamino]-3-(4''-isocarbostyriloxy)-2-propanol, and (2R, 1'R)-1-[2'-(o-methoxyphenoxy)-1'-methylethylamino]-3-(4''-isocarbostyriloxy)-2-propanol, respectively. These four optical isomers have different activities for their β-adrenergic-blocking effect and α-adrenergic-blocking effect and are useful as valuable agents for therapeutic treatment of various cardiovascular diseases, as compared to an optically inactive racemic mixture of said isomer compounds. These four optical isomers may be produced and isolated from each other by chromatographing (1'S)- or (1'R)-N-[2'-(o-methoxyphenoxy)-1'-methylethyl]-5-(4''-isocarbostyriloxymethyl)-2-oxazolidones to isolate either its (5R, 1'S)-isomer and its (5S, 1'S)-isomer, or its (5S, 1'R)-isomer and its (5R, 1'R)-isomer therefrom separately and then hydrolyzing each of these isolated isomers under alkaline conditions to obtain separately (2R, 1'S)-, (2S, 1'S)-, (2S, 1'R)- and (2R, 1'R)-1-[2'-(o-methoxyphenoxy)-1'-methylethylamino]-3-(4''-isocarbostyriloxy)-2-propanols.

4 Claims, No Drawings

OPTICALLY ACTIVE ISOCARBOSTYRIL DERIVATIVES AND A METHOD OF PREPARING THE SAME

This is a continuation-in-part of U.S. patent application No. 562,237, filed Dec. 16, 1983 now U.S. Pat. No. 4,526,893.

SUMMARY OF THE INVENTION

This invention relates to new optically active isocarbostyril derivatives and also to a method of preparing these new optically active isocarbostyril derivatives. More particularly, this invention relates to four optically active isomers of a new compound, 1-[2'-(o-methoxyphenoxy)-1'-methylethylamino]-3-(4''-isocarbostyriloxy)-2-propanol as the new substances. These four optically active isomers include specifically the (2R, 1'S)-isomer, (2S, 1'S)-isomer, (2S, 1'R)-isomer and (2R, 1'R)-isomer of 1-[2'-(o-methoxyphenoxy)-1'-methylethylamino]-3-(4''-isocarbostyriloxy)-2-propanol.

These new optically active isocarbostyril derivatives according to this invention exhibit a high β-adrenergic blocking activity and a high α-adrenergic blocking activity and are useful in therapeutic treatment of hypertension and cardiovascular diseases, including angina pectoris, arrhythmia and glaucoma.

BACKGROUND OF THE INVENTION

We, the present inventors, already found that an isocarbostyril derivative represented by the formula

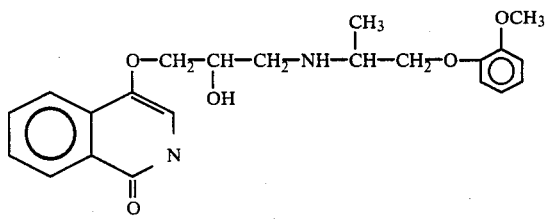

namely a compound previously named as 4-{3-[2-(2-methoxyphenoxy)-1-methylethylamino]-2-hydroxypropoxy}-isocarbostyril and now named as 1-[2'-(o-methoxyphenoxy)-1'-methylethylamino]-3-(4''-isocarboxystyriloxy)-2-propanol is a new compound which is useful as a medicinal compound for the therapeutic treatment of cardiovascular diseases (see Japanese patent application unexamined first publication "Kokai" No. 116269/84 published July 5, 1984 of Japanese patent application No. 225996/82; European patent application publication No. 0113910 A1 published July 25, 1984; pending U.S. patent application Ser. No. 562,237 filed Dec. 16, 1983, now U.S. Pat. No. 4,526,893). In the specification of these earlier patent applications, we have suggested that the particular compound mentioned above and its analogues contains two asymmetric carbon atoms in the molecule thereof and there would theoretically be a possibility that four different optical isomers should exist for said particular compound. In the past, however, actually we did not succeed in isolating independently such four optical isomers from said compound, so that detailed properties of each of such optical isomers were not yet elucidated.

Hithertobefore, it is known that a conventional optical resolution method comprising reacting any optically active chemical reagent with a compound containing asymmetric arbon atom(s) to be optically resolved is not suitable for separately obtaining or isolating the theoretically existing four optical isomers from such a compound containing two asymmetric carbon atoms in the molecule thereof. For the purpose of isolating the theoretically existing four optical isomers separately or independently from a compound containing two asymmetric carbon atoms in the molecule, therefore, there has usually been adopted in the prior art a method which comprises preparing synthetically, in a first stage, said compound in the form of a mixture of two optical isomers (diastereomers) where the first of the two asymmetric carbon atoms present has, initially, a predetermined particular configuration, (R) or (S), while the second of the two asymmetric carbon atoms may have the configuration (R) or the configuration (S) in the respective molecules of the isomers, namely in the form of the mixture of such two diastereomers which are assumed so from the stand-point of the second one of the two asymmetric carbon atoms. Then the compound as prepared in the first stage as a mixture of two diastereomers is subjected to fractional crystallization or other optical resolution methods to isolate said two diastereomers from each other. In a further step, said compound in the form of a mixture of the further two diastereomers where the first one of the two asymmetric carbon atoms present here has initially a predetermined particular configuration (S) or (R), other than that shown by the first asymmetric carbon atom of the first-prepared two diastereomers. However, the second asymmetric carbon atom may have the configuration (R) or (S) in the respective molecules of the further two diastereomers. Lastly the compound as prepared in the aforesaid further stage as the further mixed two diastereomers is subjected to fractional crystallization or other optical resolution methods to isolate said further two diastereomers from each other so that the four different optically active isomers are isolated from each other are ultimately afforded.

With the compound of the formula

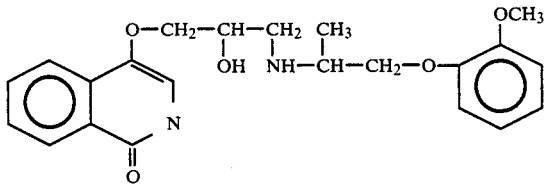

theoretically, it may appear to be equally possible that four different optically active isocarbostyrils in the form of the (S-S)-isomer, (S-R)-isomer, (R-S)-isomer and (R-R)-isomer, respectively, represented by a general formula (II):

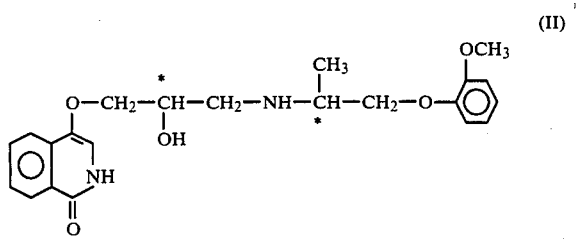

wherein the asterisks * each denote either the (S)-configuration or (R)-configuration and more exactly, each carbon atom having the asterisk * attached thereto as shown exhibits either the (S)-configuration or the (R)-configuration are isolated from each other and thus obtained according to the prior art method as acknowledged just above. For instance, if the compound represented by the formula (III):

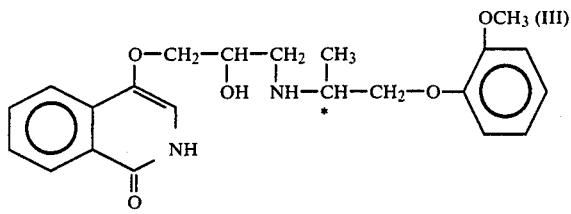

wherein the asterisk * denotes a predetermined particular one of the (S)-configuration and (R)-configuration, can be prepared in a first stage as the mixed two diastereomers which are assumed so from the stand-point of the second asymmetric carbon atom having no asterisk attached thereto, followed by isolating these mixed two diastereomers into each independently existing diastereomer by any suitable optical resolution method, then, in theory the compound of the formula (III) where the asymmetric carbon atom having the asterisk attached thereto as shown exhibits here the (R)- or (S)-configuration other than that of the compound (III) diastereomers as prepared in the first stage, can subsequently be prepared in a further stage as the further mixed two diastereomers, followed by isolating said further mixed two diastereomers into each independently existing diastereomer by any suitable optical resolution method.

Actually, however, as far as the present inventors have tested in various ways, the compounds of the formula (III) themselves obtained as the mixed two diastereomers cannot be isolated into an independently existing single diastereomer by subjecting them to various conventional optical resolution methods which include, for example, fractional crystallization or different chromatographic methods and the like.

As a result of our further research, we have now found that when the compound of the formula (III) has once been converted into an oxazolidone derivative represented by the formula (I):

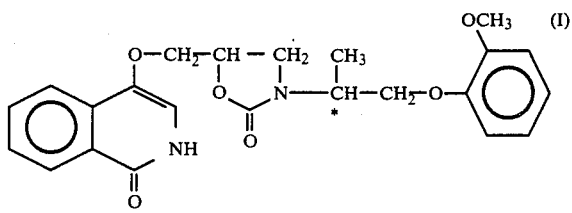

wherein the first asymmetric carbon atom having the asterisk attached thereto as shown exhibits either the (S)-configuration or the (R)-configuration and wherein the second asymmetric carbon atom having no asterisk attached thereto may exhibit the (R)-configuration or the (S)-configuration, this oxazolidone derivative (I) obtained as the mixed two diastereomers can easily be isolated into its independently existing single diastereomers by a conventional isolation technique, for example, chromatography, including liquid chromatography, column chromatography and other chromatographic procedures. When the oxazolidone derivative of the formula (I) is isolated into its independently existing single diastereomers, followed by hydrolyzing each single diastereomer to give the corresponding actually active 1-[2'-(o-methoxyphenoxy)-1'-methylethylamino]-3-(4''-isocarbostyriloxy)-2-propanol generically represented by the general formula (II), there can be afforded the four different optically active isocarbostyril derivatives as specified above and represented by the general formula (II), each in the form of an independently isolated new substance.

DETAILED DESCRIPTION OF THE INVENTION

According to a first aspect of this invention, there is provided as the new substance an optically active isocarbostyril derivative in the form of (S-S)-isomer, (S-R)-isomer, (R-S)-isomer or (R-R)-isomer and represented by the formula (II):

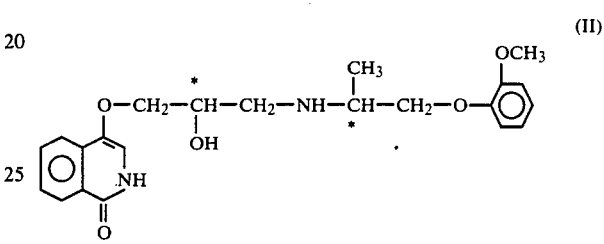

wherein the asymmetric carbon atoms each having the asterisk attached thereto as shown exhibit either the (S)-configuration or the (R)-configuration, or a pharmaceutically acceptable acid addition salt of said isocarbostyril derivative.

The optically active isocarbostyril derivative of the formula (II) according to the invention includes the following compounds specified in Table 1 below:

TABLE 1

| Compound No. | |
|---|---|
| (1) | (2R, 1'S)-1-[2'-(o-methoxyphenoxy)-1'-methylethylamino]-3-(4''-isocarbostyriloxy)-2-propanol |
| (2) | (2S, 1'S)-1-[2'-(o-methoxyphenoxy)-1'-methylethylamino]-3-(4''-isocarbostyriloxy)-2-propanol |
| (3) | (2S, 1'R)-1-[2'-(o-methoxyphenoxy)-1'-methylethylamino]-3-(4''-isocarbostyriloxy)-2-propanol, and |
| (4) | (2R, 1'R)-1-[2'-(o-methoxyphenoxy)-1'-methylethylamino]-3-(4''-isocarbostyriloxy)-2-propanol. |

The isolated four optical isomers specified above are each obtained in the form of a colorless crystalline substance having the physico-chemical properties are detailed in Examples 7-8 given hereinafter.

The new optically active isocarbostyril derivatives of this invention may be converted into their pharmaceutically acceptable acid addition salts by reacting with a pharmaceutically acceptable inorganic acid such as hydrochloric, hydrobromic, sulfuric and phosphoric acid, or with a pharmaceutically acceptable organic acid such as acetic, citric, maleic, benzoic, oxalic and tartaric acids, and the like according to conventional salt-forming techniques.

According to a second aspect of this invention, there is provided a process of producing the isolated four optically active isocarbostyril derivatives having the (S-S)-configuration, the (S-R)-configuration, (R-S)-configuration and (R-R)-configuration, respectively, for the two asymmetric carbon atoms present therein and represented by the general formula (II):

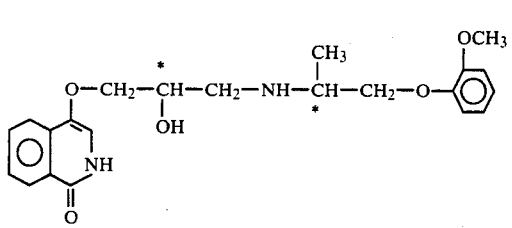

(II)

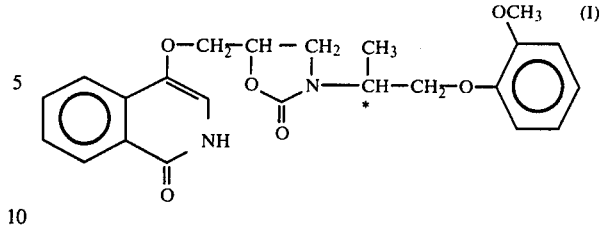

(I)

wherein the asymmetric carbon atoms each having the asterisk attached thereto exhibit either the (S)-configuration or the (R)-configuration, which comprises optically resolving the diastereomers of the oxazolidone compound represented by the formula (I):

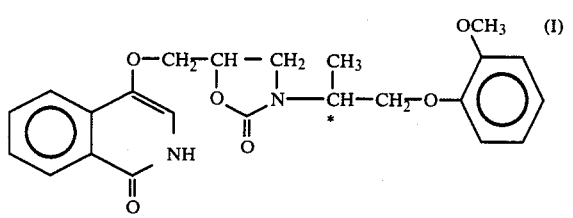

(I)

wherein the asterisked asymmetric carbon atoms as shown exhibits either the (S)-configuration or the (R)-configuration, by a chromatographic method, to obtain the four different optical isomers of the oxazolidone compound independently from each other, and then hydrolyzing the respective optical isomers separately to produce independently the (2R, 1′S)-isomer, (2S, 1′S)-isomer, (2S, 1′R)-isomer and (2R, 1′R)-isomer of the resulting 1-[2′-(o-methoxyphenoxy)-1′-methylethylamino]-3-(4″-isocarbostyriloxy)-2-propanol as represented by the formula (II).

In the another way, the process of the second aspect of this invention may particularly be described as a process of producing four optically active isomers, i.e., (2R, 1′S)-isomer, (2S, 1′S)-isomer, (2S, 1′R)-isomer and (2R, 1′R)-isomer of 1-[2′-(o-methoxyphenoxy)-1′-methylethylamino]-3-(4″-isocarbostyriloxy)-2-propanol as isolated from each other and represented by the general formula (II):

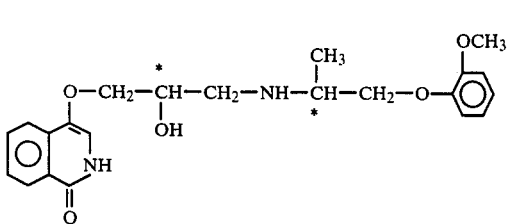

(II)

wherein the asymmetric carbon atoms each having the asterisk attached thereto as shown exhibit either the (S)-configuration or the (R)-configuration in each isomer, which process comprises (a) providing the oxazolidone compound represented by the formula (I):

wherein the asterisk * denotes that the first asymmetric carbon atom having the asterisk attached thereto as shown exhibits either the (S)-configuration or the (R)-configuration and wherein the second asymmetric carbon atom having no asterisk attached thereto exhibits the (S)-configuration or the (R)-configuration, as a first mixture of two diastereomers of said oxazolidone compound where the asterisked first asymmetric carbon atoms exhibits a particular one of the (S)- and (R)-configurations and the non-asterisked second asymmetric carbon atoms exhibits the (S)-configuration or the (R)-configuration in the respective molecules of these two diastereomers, and also as a second mixture of the further two diastereomers where the asterisked first asymmetric carbon atom exhibits the other particular (R)-configuration or (S)-configuration than that exhibited by the first asymmetric carbon atom of the two diastereomers of said first mixture and the non-asterisked second asymmetric carbon atom exhibits the (S)-configuration or the (R)-configuration in the respective molecules of the further two diastereomers of said second mixture, said first mixture being provided separately from the said second mixture of the diastereomers, (b) subjecting said first mixture of the two diastereomers and said second mixture of the further two diastereomers separately to optical resolution by a chromatographic method to give independently isolated four diastereomers or optical isomers, namely (5R, 1′S)-N-[2′-(o-methoxyphenoxy)-1′-methylethyl]-5-(4″-isocarbostyriloxymethyl)-2-oxazolidone, (5S, 1′S)-N-[2′-(o-methoxyphenoxy)-1′-methylethyl]-5-(4″-isocarbostyriloxymethyl)-2-oxazolidone, (5S, 1′R)-N-[2′-(o-methoxyphenoxy)-1′-methylethyl]-5-(4″-isocarbostyriloxymethyl)-2-oxazolidone and (5R, 1′R)-N-[2′-(o-methoxyphenoxy)-1′-methylethyl]-5-(4″-isocarbostyriloxymethyl)-2-oxazolidone as isolated from each other, and (c) hydrolyzing these four optical isomers separately to produce independently the (2R, 1′S)-isomer, the (2S, 1′S)-isomer, the (2S, 1′R)-isomer and the (2R, 1′R)-isomer of the 1-[2′-(o-methoxyphenoxy)-1′-methylethylamino]-3-(4″-isocarbostyriloxy)-2-propanol formed as the hydrolysis product.

Particularly, the two diastereomers of said first mixture which are initially provided in this process may consist of (1′S)-N-[2′-(o-methoxyphenoxy)-1′-methylethyl]-5-(4″-isocarbostyriloxymethyl)-2-oxazolidones, while the two diastereomers of said second mixture may consists of (1′R)-N-[2′-(o-methoxyphenoxy)-1′-methylethyl]-5-(4″-isocarbostyriloxymethyl)-2-oxazolidones, or vice versa.

The optically active isocarbostyril derivatives of the formula (II) according to this invention may be produced via a synthetic route which starts from 4-(2,3-epoxypropyloxy)-isocarbostyril of the formula (IV) and (S)- or (R)-B 1-(o-methoxyphenoxy)-2-aminopropane of the formula (V) shown below and is depicted by the following reaction scheme-I.

REACTION SCHEME I

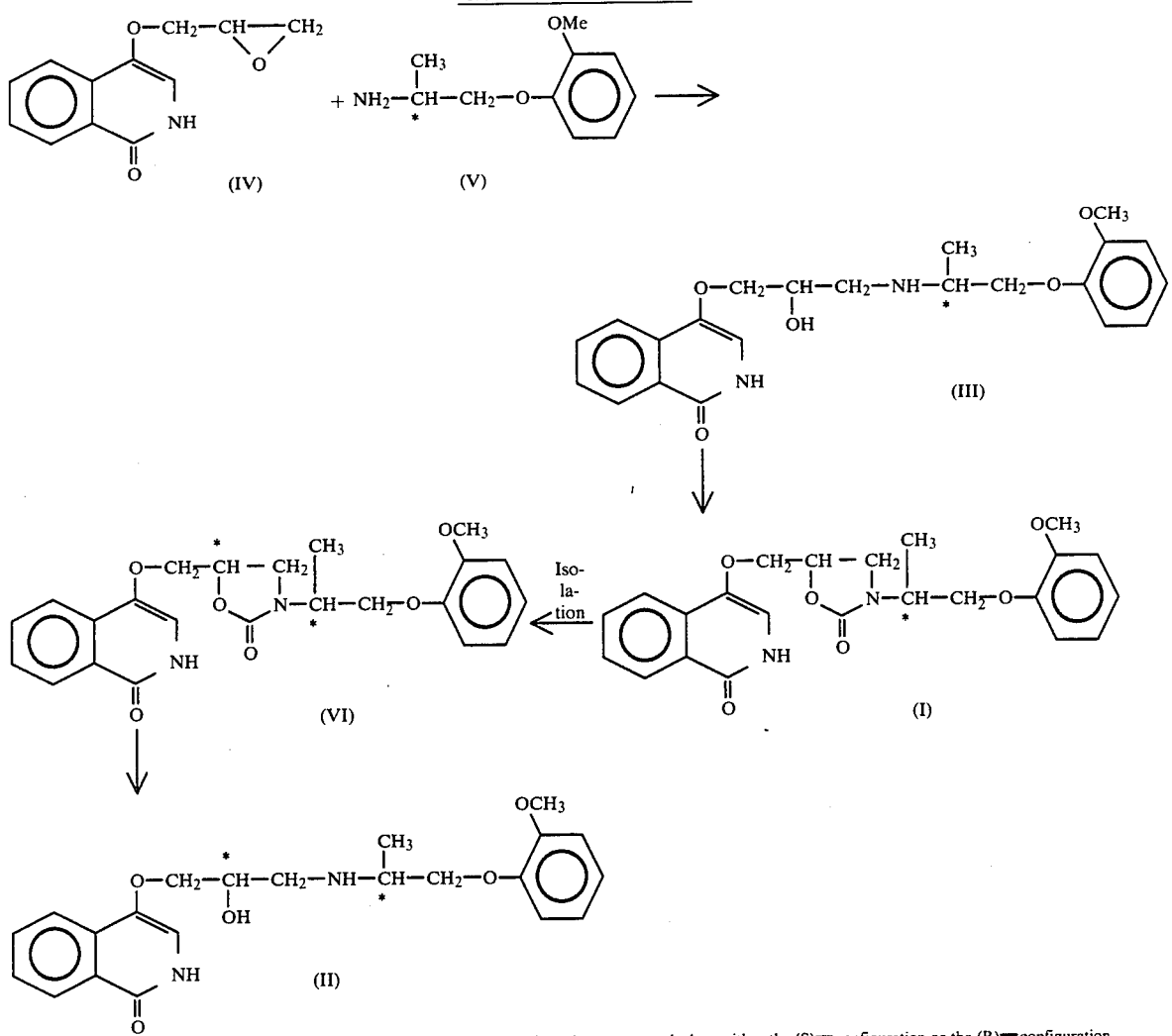

In this reaction scheme I, the asterisk * denotes that the asterisked asymmetric carbon atoms each show either the (S)—configuration or the (R)—configuration.

With reference to the reaction scheme-I above, the reaction of 4-(2',3'-epoxypropyloxy)-isocarbostyril of the formula (IV) with (S)- or (R)-1-(o-methoxyphenoxy)-2-aminopropane of the formula (V) can be carried out at a temperature of from room temperature to approximately 100° C. This reaction will usually be completed after a time of several hours to approximately 20 hours. The compound (V) is usually used in a proportion of more than 1 mol. and preferably of approximately 1.5 to 3 mol. per 1 mol. of the compound (IV). The solvent used as the reaction medium may be methanol, ethanol, ethylether, benzene and the like, for example.

The condensation reaction of the compounds (IV) with the compound (V) produces 1-[2'-(o-methoxyphenoxy)-1'-methylethylamino]-3-(4"-isocarbostyriloxy)-2-propanol of the formula (III) wherein the asterisked carbon atom exhibits either the (S)-configuration or the (R)-configuration. The compound of the formula (III) is usually obtained as a mixture of the two diastereomers which are assumed so from the standpoint of the non-asterisked second asymmetric carbom atom at the 2-position of this propanol compound (III), respectively, for the (S)-isomer and the (R)-isomer of the aminopropane compound (V) as employed. The mixed two diastereomers of the compound (III) are then converted into the oxazolidone compound of the formula (I) by heating at an elevated temperature in the presence of e.g., ethyl trichloroacetate. The oxazolidone compound (I) formed as the mixed two diastereomers are subsequently isolated into independently existing single diastereomers by a conventional isolation technique such as chromatography. In this way, the four different optical isomers of the oxazolidone compound represented by the formula (VI) can be ultimately obtained, each in the isolated state. When these four optical isomers (VI) are hydrolyzed independently under alkaline conditions, there are independently afforded four different optical isomers of the isocarbostyril derivative represented by the formula (II) which have respectively the (S-S)-configuration, (S-R)-configuration, (R-S)-configuration and (R-R)-configuration in respect of the two asymmetric carbon atoms present in the molecule thereof.

The reaction for conversion of the compound of the formula (III) into the compound of the formula (I) may successfully be achieved in the presence of ethyl trichloroacetate, although this conversion may also be conducted in the presence of phosgene, a chloroformic acid ester or a carbonic acid di-ester.

The reaction for conversion of the compound (III) into the compound (I) may be carried out at a temperature of from 50° C. to 200° C. and preferably from 100° C. to 150° C., and this reaction can be completed after a reaction time of several minutes to 5 hours. The reaction can usually be effected in the presence of a large excess of ethyl trichloroacetate and optionally, together with an organic solvent such as toluene, xylene, dimethylsulfoxide, dimethylformamide, diglyme and the like.

The isolation of the resulting mixed two diastereomers of the compound of the formula (I) into each single diastereomer may be achieved by a conventional isolation technique such as solvent extraction, fractional crystallization or precipitation. However, it is preferred to perform said isolation of the mixed diastereomers from each other according to a chromatographic method. For example, gas chromatography, liquid chromatography, column chromatography, thin layer chromatography or other chromatographic procedures may be utilized with advantage.

For instance, when said isolation of the mixed diastereomers (I) is effected according to a liquid chromatography using a forward phase column such as silica gel, the development solvent used therefor may comprise a less polar organic solvent such as hexane, benzene, chloroform and methylene chloride which contains several percentages to several tens of percentages (by volume) of a polar organic solvent such as methanol, ethanol, propanol, butanol, ethyl acetate and acetone.

When the liquid chromatography is effected using a reversed phase column such as silanized silica gel, $C_{18}$-silica gel, $C_8$-silica gel, the development solvent used therefor may be an aqueous solution containing several percentages to several tens of percentages of at least one of organic solvents such as acetonitrile, methanol, ethanol, propanol, acetic acid, tetrahydrofuran and 1,4-dioxane.

When a thin layer chromatography is conducted for the above-mentioned isolation purpose, the absorption medium used may be any of the ones of the forward phase type and the reversed phase type similarly to the case of the liquid chromatography. The available development solvent for the thin layer chromatography may be the same as those used for the liquid chromatography.

When the four different optical isomers of the oxazolidone compound represented by the formula (VI) are independently hydrolyzed under alkaline conditions, there are independently yielded the corresponding four different optical isomers of the isocarbostyril-substituted propanol compound represented by the formula (II). The hydrolysis can be effected in the presence of an excess of alkali, for example, an alkali metal carbonate, bicarbonate or hydroxide such as sodium carbonate, sodium bicarbonate, potassium carbonate, sodium hydroxide and potassium hydroxide, and in an aqueous reaction medium comprising a proportion of several percentages to several tens of percentages and preferably of 10 to 20% (by volume) of an alkanol type solvent such as methanol and ethanol or an ether type solvent such as tetrahydrofuran and 1,4-dioxane. The hydrolysis can be carried out at a temperature of from room temperature to 100° C., normally under conditions.

The compound of the formula (IV) used in the synthetic route of the reaction scheme-I shown hereinbefore may be prepared by the reaction of the following reaction scheme-II:

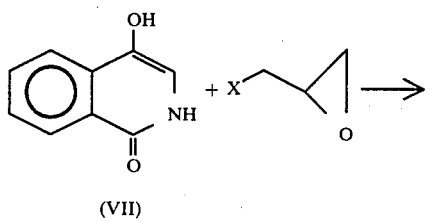

(VII)

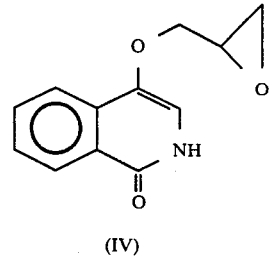

(IV)

wherein X stands for a halogen atom such as chlorine, bromine and iodine, or a reactive group, for example, a tosyl or methanesulfonyl group.

The production of the compound of the formula (IV) from the 4-hydroxyisocarbostyril compound of the formula (VII) can be performed in the presence of alkali and using the reactant selected from epichlorohydrin, epibromohydrin, epi-iodohydrin, 3-tosyl-1,2-epoxypropane, 3-methanesulfonyl-1,2-epoxypropane and other functionally equivalent compounds. Epibromohydrin can successfully be used in a proportion of 1.5 to 3 mol. per mol. of the compound (VII). The alkali available for this purpose includes sodium hydride, potassium tert-butoxide, sodium methylate, sodium carbonate, potassium carbonate, sodium hydroxide, potassium hydroxide and the like.

The reaction medium used for the reaction of producing the compound (IV) can comprise an alkanol type solvent such as methanol and ethanol, an aqueous alkanol solvent, a polar, aprotic organic solvent such as dimethylsulfoxide and dimethylformamide and/or such a polar, aprotic organic solvent containing water. The reaction of producing the compound (IV) can be effected at a temperature of approximately 0° C. to 150° C. and can normally be carried out at a temperature of room temperature to 50° C. with favorable results. It takes a reaction time of from several hours to several tens hours.

The (S)- or (R)-1-(o-methoxyphenoxy)-2-aminopropane compound of the formula (V) used in the synthetic route of the reaction scheme-I may be prepared according to a method which is depicted by the following reaction scheme-III:

REACTION SCHEME-III

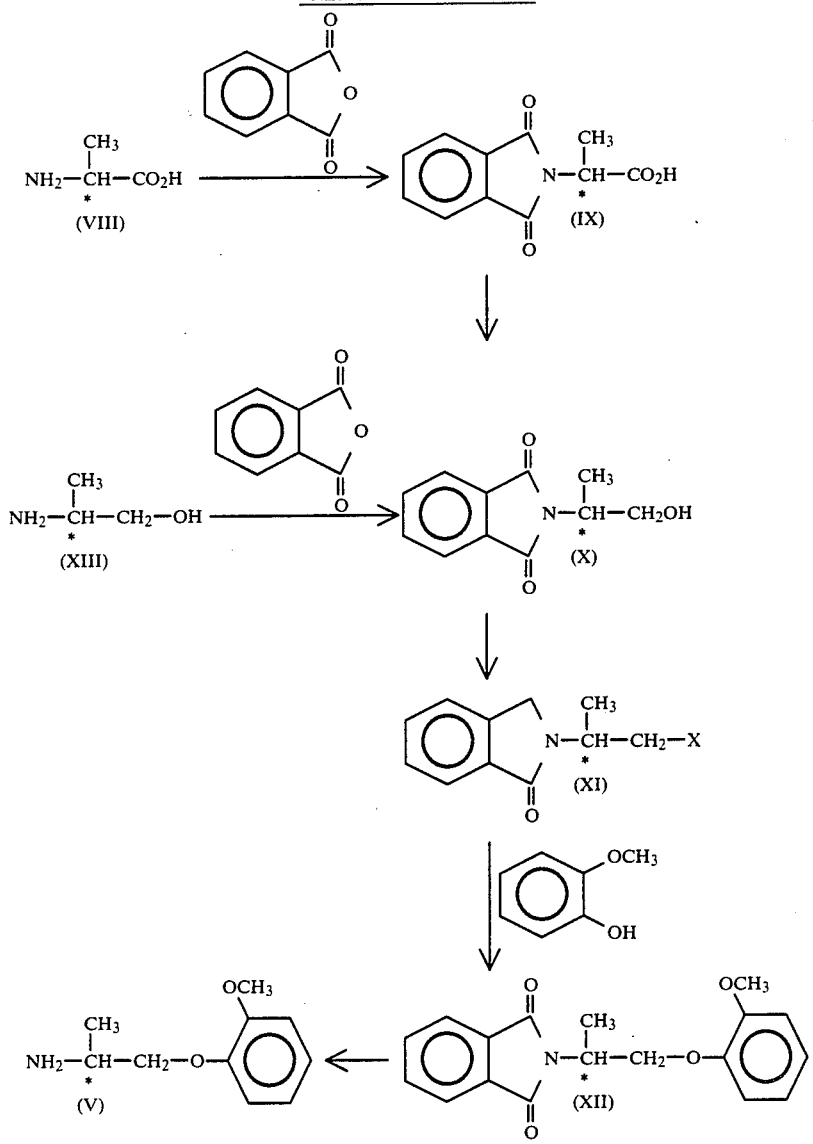

where X stands for a halogen atom, or a reactive group such as a tosyl and methanesulfonyl group, and the asterisked asymmetric carbon atom exhibits either the (R)-configuration or the (S)-configuration.

As will be clear from the reaction scheme-III, the S(+)-amine compound represented by the formula (V) where the asterisk * stands for the (S)-configuration of the asterisked asymmetric carbon atom may be synthesized from L(S)-alanine of the formula (VIII), while the R(−)-amine compound of the formula (V) where the asterisk * stands for the (R)-configuration of the asterisked asymmetric carbon atom here may be synthesized from D(R)-alanine of the formula (VIII).

Alternatively, (S)- or (R)-aminopropanol of the formula (XIII) may be used as an initial raw material to give the amine compound of the formula (V) having the corresponding steric configuration.

When the L(S)-alanine of the formula (VIII) is reacted with phthalic anhydride, there is formed a compound of the formula (IX). This reaction can normally be achieved accomplished by reacting the compound (VIII) with phthalic anhydride in equi-molar proportions at an elevated temperature of 100° C. to 180° C. but in the absence of any solvent. The reaction can be completed after a time of several tens of minutes to approximately 2 hours.

The reductive conversion of the carboxylic acid compound of the formula (IX) into the alcohol compound of the formula (X) can be achieved by reacting with a reducing agent of the metal hydride type, for example, sodium borohydride, lithium borohydride, lithium auminum hydride, diborane and the like. This reduction reaction can be carried out at a temperature of approximately 0° C. to 50° C. and is completed after a time of several tens of minutes to several hours.

The compound of the formula (X) can alternatively be prepared by reacting an aminopropanol of the formula (XIII) with phthalic anhydride in equi-molar proportions at an elevated temperature of approximately 100° C. to 180° C. for a time of several tens of minutes to several hours but in the absence of any solvent.

When the compound of the formula (X) is either halogenated with a halogenation reagent such as $PBr_3$, SOCl₂, PCl₃ or sulfonylated with a sulfonylation reagent such as tosyl chloride and methanesulfonyl chloride, there is derived therefrom the corresponding compound of the formula (XI).

When the compound (X) is halogenated, the halogenation reaction can be effected either in the absence of any solvent or in the presence of an inert organic solvent such as ethyl ether, tetrahydrofuran, isoproyl ether, benzene and chloroform and optionally, in the additional presence of a basic compound such as pyridine or triethylamine as the catalyst. The halogenation reaction can be completed after a time of several tens of minutes to several hours at a reaction temperature of approximately 0° C. to 50° C.

When the compound (X) is sulfonylated by reacting with a reagent such as methanesulfonyl chloride and tosyl chloride, the sulfonylation reaction can be effected in the presence of a basic organic solvent such as pyridine or triethylamine. The basic organic solvent can optionally be admixed with a further inert organic solvent such as tetrahydrofuran, ethyl ether and benzene. This reaction may be carried out at a temperature of approximately 0° C. to 50° C. and finished in a time of several hours to approximately 20 hours.

When the product compound of the formula (XI) is then reacted with guaiacol (i.e., o-methoxyphenol), there is formed the compound of the formula (XII). The reaction of the compound (XI) with guaiacol can be accomplished in such a manner that guaiacol is firstly reacted with an alkali metal base such as sodium hydroxide, potassium hydroxide, potassium carbonate, sodium carbonate, sodium tert-butoxide, potassium tert-butoxide to form an alkali metal salt of guaiacol, and this guaiacol alkali metal salt is then reacted with the compound of the formula (XI) as added. The reaction medium used for this condensation reaction can comprise an organic solvent such as methanol, ethanol, ethyl ether, tetrahydrofuran, acetone, dimethylsulfoxide and dimethylformamide, and/or aqueous ones of such organic solvents. The reaction can be carried out at a reaction temperature of from ambient temperature to approximately 100° C. and finished in a time of from several hours to approximately 20 hours.

When the resulting compound of the formula (XII) is hydrolyzed, there is obtained the aimed for compound of formula (V). The hydrolysis of the compound (XII) may be effected in the presence of an alkali metal hydroxide such as sodium hydroxide and potassium hydroxide. However, the hydrolysis can successfully be achieved in the presence of an excess of hydrazine.

The reaction medium for the hydrolysis can suitably be water, or an aqueous lower alkanol such as aqueous methanol and aqueous ethanol. The hydrolysis reaction can be carried out at a temperature of from ambient temperature to approximately 100° C. and normally under heating and refluxing. The reaction can be completed after a time of from several tens of minutes to several hours.

The four different optically active isocarbostyril derivatives of this invention represented by the generic formula (II) each have a high β-adrenergic blocking activity and a high α-adrenergic blocking activity. The ratio of the degree of the β-adrenergic blocking activity to the degree of the α-adrenergic blocking activity shown by the compound varies for every four optical isomers of the compound (II), so that each these four optical isomers are considered to be a more valuable drug, as compared to racemic mixtures of the compound (II).

The optically active isocarbostyril derivatives of this invention according to the formula (II) have the biological properties as summarized in Table 2 given below.

1. β-Adrenergic blocking effect

This effect was estimated by evaluating the activity of the new optically active isomers of this invention which antagonizes an increase in the beating rate of an isolated right atrium of a guinea pig induced by isoproterenol. The efficacy of the β-blocking activity of the respective optical isomers of the formula (I) was estimated in terms of the $pA_2$ value as assessed according to the method of Van Bossum (see Van Bossum, "Arch. int. Pharmacodyn. Ther." Vol. 143, page 299 (1963)).

2. α-Adrenergic blocking effect

This effect was estimated by evaluating the activity of the new optically active isomers of this invention which inhibits a contraction of an isolated anococcygeal muscle of a rat induced by noradrenaline.

The efficacy of the α-blocking activity of the test compounds was estimated in terms of the $pA_2$ value as assessed.

The test results obtained are shown in Table 2 below. The test compounds are of the following formula:

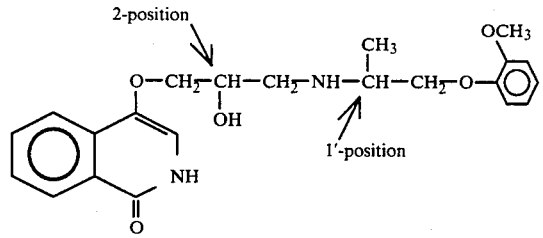

TABLE 2

| Compound No. | Configuration | | α-Blocking activity ($pA_2$ value) | β-Blocking activity ($pA_2$ value) |
|---|---|---|---|---|
| | 2-Positioned asymmetric carbon atom | 1'-Positioned asymmetric carbon atom | | |
| A | racemic (R,S) | racemic (R,S) | 5.56 | 7.97 |
| No. 1 | (R)-configuration | (S)-configuration | 4.88 | 6.23 |
| No. 2 | (S)-configuration | (S)-configuration | 4.68 | 7.24 |
| No. 3 | (S)-configuration | (R)-configuration | 5.61 | 8.58 |
| No. 4 | (R)-configuration | (R)-configuration | 5.95 | 6.98 |

The Compound Nos. mentioned in Table 2 above have been referred to in Table 1 hereinbefore, excepting that "Compound No. A" stands for the compound which is described as the final product in Example 10 of the specification of European patent application publication No. 0113910 A1 or the pending U.S. patent application Ser. No. 562,237.

The respective four optical isomers as isolated of the oxazolidone compound of the formula (VI) are also the new substances and hence are also the subject of this invention.

The following Examples further illustrate, but not limit, this invention.

EXAMPLE 1

A solution in methanol of 28% sodium methoxide (71 cc) was added dropwise to a solution of 4-hydroxyisocarbostyril (54.5 g) in methanol (400 ml) at room temperature, to which was then added epibromohydrin (139 g). The resulting mixture was then heated at 50° C. for 2 hours under stirring.

The reaction solution thus formed was poured into ice-water, followed by extraction with chloroform. The chloroform extract was dried and concentrated and the concentrate as a crude reaction product was chromatographed on a silica gel column with chloroform-methanol as eluent, yielding 4-(2',3'-epoxypropyloxy)-isocarbostyril (17.4 g).

This product (17.4 g) and (S)-1-(o-methoxyphenoxy)-2-aminopropane (42.3 g) are added to ethanol (500 ml), and the resultant mixture was heated under reflux for 2 hours.

The resulting reaction solution was concentrated in vacuo and the concentrate was chromatographed on a silica gel column with chloroform-methanol as eluent, affording (1'S)-1-[2'-(o-methoxyphenoxy)-1'-methylethylamino]-3-(4"-isocarbosytriloxy)-2-propanol (25.1 g; 18.6%) of formula (1):

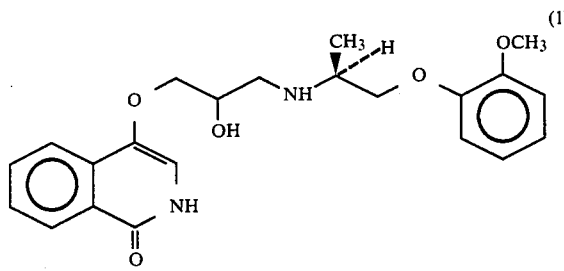

(1)

$[\alpha]_D^{20} = +8.75°$ (c=1, CHCl$_3$—MeOH (9:1)).
IR (liquid film): 1660, 1605, 1590 cm$^{-1}$.
NMR(d-6 DMSO, δ): 1.10 (3H, d, J=7 Hz), 2.5–3.1 (3H), 3.71 (3H, s), 3.7–4.2 (5H), 6.7–8.3 (10H).

EXAMPLE 2

The procedure of Example 1 was repeated except that (R)-1-(o-methoxyphenoxy)-2-aminopropane was used in place of the (S)-1-(o-methoxyphenoxy)-2-aminopropane. There was thus obtained (1'R)-1-[2'-(o-methoxyphenoxy)-1'-methylethylamino]-3-(4"-isocarbostyriloxy)-2-propanol of formula (2). Yield was 23% based on the amount of 4-hydroxyisocarbostyril used.

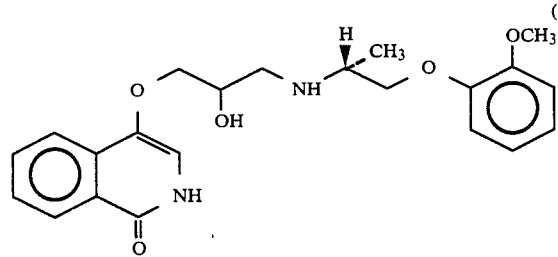

(2)

$[\alpha]_D^{20} = -6.67°$ (c=1, CHCl$_3$—MeOH (9:1)).
IR (liquid film): 1660, 1605, 1590 cm$^{-1}$.
NMR(d-6 DMSO, J): 1.10 (3H, d, J=7 Hz), 2.5–3.1 (3H), 3.71 (3H, s), 3.7–4.2 (5H), 6.7–8.3 (10H).

EXAMPLE 3

(1'S)-1-[2'-(o-Methoxyphenoxy)-1'-methylethylamino]-3-(4"-isocarbostyriloxy)-2-propanol (0.85 g) of formula (1) above was added to ethyl trichloroacetate (9 cc), and the resulting mixture was heated under an argon stream at 110° C. for 4 hours.

The resulting reaction solution was distilled in vacuo to remove any excess ethyl trichloroacetate, and the residue was chromatographed on a silica gel column with chloroform-ethanol as eluent to yield (1'S)-N-[2'-(o-methoxyphenoxy)-1'-methylethyl]-5-(4"-isocarbostyriloxymethyl)-2-oxazolidone (0.63 g; 69.6%) of formula (3):

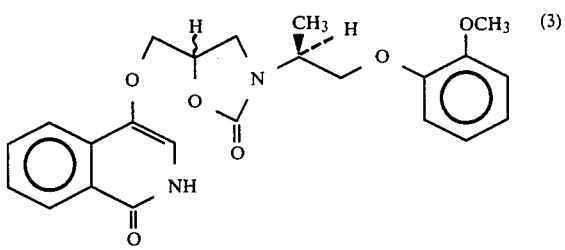

IR(CHCl$_3$): 1745, 1650, 1605, 1590 cm$^{-1}$.
NMR(CDCl$_3$, δ): 1.38 (3H, d, J=7 Hz), 3.61 (1.5H, s), 3.75 (1.5H, s), 3.7–4.5 (7H), 4.8 (1H, m), 6.6–8.4 (10H).

EXAMPLE 4

The procedure of Example 3 was repeated but starting with (1'R)-1-[2'-(o-methoxyphenoxy)-1'-methylethylamino]-3-(4"-isocarbostyriloxy)-2-propanol (510 mg) of formula (2) above, and there was obtained (1'R)-N-[2'-(o-methoxyphenoxy)-1'-methylethyl]-5-(4"-isocarbostyriloxymethyl)-2-oxazolidone (440 mg; 81%) of formula (4):

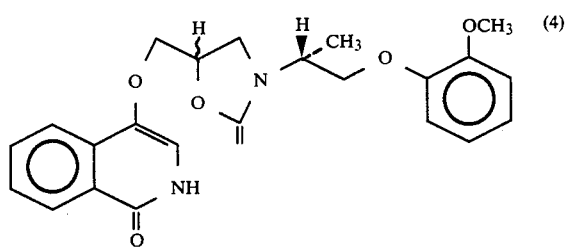

IR(CHCl$_3$): 1745, 1650, 1605, 1590 cm$^{-1}$.
NMR(CDCl$_3$, δ): 1.38 (3H, d, J=7 Hz), 3.61 (1.5H, s), 3.75 (1.5H, s), 3.7–4.5 (7H), 4.8 (1H, m), 6.6–8.4 (10H).

EXAMPLE 5

(1'S)-N-[2'-(o-methoxyphenoxy)-1'-methylethyl]-5-(4"-isocarbostyriloxymethyl)-2-oxazolidone (0.40 g) of formula (3) above was chromatographed in a column of ODS-Q3 (24 mmφ×360 mm) (a packed column RQ-2 made by Wako.Junyaku Kogyo K.K.). Elution was effected with acetonitrile-methanol-water (3:2:4 by volume) as eluent at a flow rate of 6 ml/min. After the elution of about 35 minutes, there was obtained (5R,1'S)-N-[2'-(o-methoxyphenoxy)-1'-methylethyl]-5-(4"-isocarbostyriloxymethyl)-2-oxazolidone (0.19 g) of formula (5) shown below. Then, after elution for a further 50 minutes, there was collected (5S,1'S)-N-[2'-(o-methoxyphenoxy)-1'-methylethyl]-5-(4"-isocarbostyriloxymethyl)-2-oxazolidone (0.13 g) of formula (6) shown below.

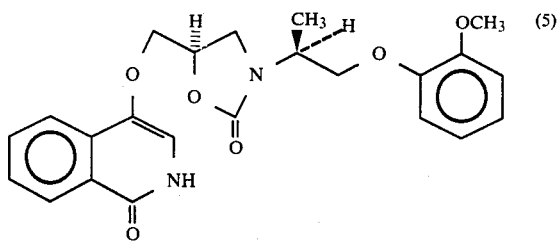

NMR(d-6 DMSO, δ): 1.38 (3H, d, J=7 Hz), 3.62 (3H, s), 3.7-4.5 (7H), 4.8 (1H, m), 6.6-8.4 (10H).

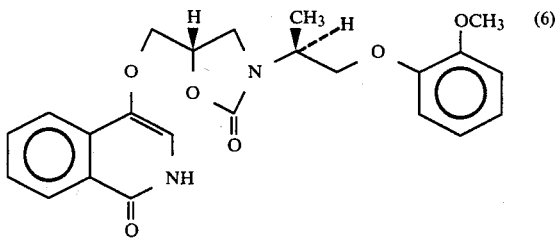

NMR(CDCl₃, δ): 1.38 (3H, d, J=7 Hz), 3.75 (3H, s), 3.7-4.5 (7H), 4.8 (1H, m), 6.6-8.4 (10H).

EXAMPLE 6

(1'R)-N-[2'-(o-methoxyphenoxy)-1'-methylethyl]-5-(4''-isocarbostyriloxymethyl)-2-oxazolidone (1.00 g) of formula (4) above was chromatographed in the same manner as that found in Example 5. There were thus collected (5S,1'R)-N-[2'-(o-methoxyphenoxy)-1'-methylethyl]-5-(4''-isocarbostyriloxymethyl)-2-oxazolidone (0.40 g) of formula (7) shown below and (5R,1'R)-N-[2'-(o-methoxyphenoxy)-1'-methylethyl]-5-(4''-isocarbostyriloxymethyl)-2-oxazolidone (0.40 g) of formula (8) shown below.

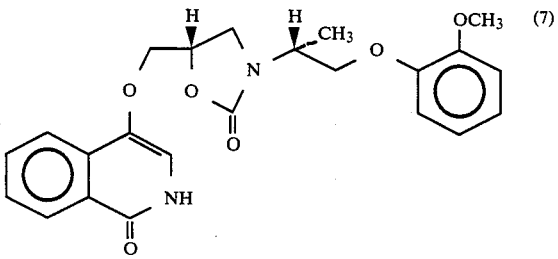

NMR(CDCl₃, δ): 1.37 (3H, d, J=7 Hz), 3.60 (3H, s), 3.7-4.5 (7H), 4.8 (1H, m), 6.6-8.4 (10H).

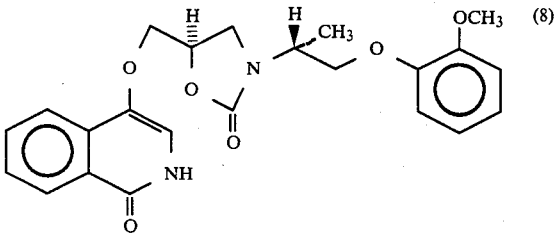

NMR(CDCl₃, δ): 1.38 (3H, d, J=7 Hz), 3.73 (3H, s), 3.7-4.5 (7H), 4.8 (1H, m), 6.6-8.4 (10H).

EXAMPLE 7

(5R,1'S)-N-[2'-(o-Methoxyphenoxy)-1'-methylethyl]-5-(4''-isocarbostyriloxymethyl)-2-oxazolidone (70 mg) of formula (5) above was heated in 70% aqueous ethanol (water containing 70% by volume of ethanol) containing 10% sodium hydroxide under reflux for 3 hours.

The resulting reaction solution was diluted with water and then extracted with chloroform. The extract in chloroform was dried and then distilled to remove the chloroform. The residue was chromatographed on a silica gel column with chloroform-methanol as eluent, yielding (2R,1'S)-1-[2'-(o-methoxyphenoxy)-1'-methylethylamino]-3-(4''-isocarbostyriloxy)-2-propanol (39 mg; 59%) of formula (9) shown below. This compound was crystallized from acetone-ether to afford white crystals.

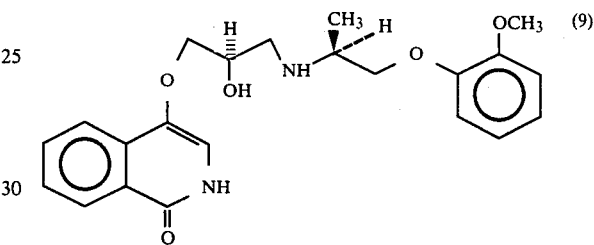

M.P. 107.6°-110.7° C.

[α]_D^{20} = +12.8° (c=1, CHCl₃—MeOH(4:1)).

NMR(CDCl₃, δ): 1.15 (3H, d, J=7 Hz), 3.76 (3H, s), 2.7-3.4 (3H), 3.6-4.3 (5H), 6.6-8.4 (10H).

EXAMPLE 8

Following the procedure of Example 7, three runs (i), (ii) and (iii) were effected wherein each of the oxazolidones of formulae (6), (7) and (8) above was used in place of that of formula (5), and yielded the corresponding optical isomer of 1-[2'-(o-methoxyphenoxy)-1'-methylethylamino]-3-(4''-isocarbostyriloxy)-2-propanol of formula (10), (11) or (12) as shown below.

(i) (2S,1'S)-isomer of Formula (10); Yield: 76.7%

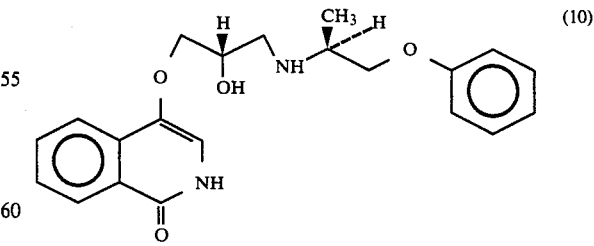

M.P. 150.1°-153.3° C.

[α]_D^{20} = +1.4° (c=1, CHCl₃—MeOH(4:1)).

NMR(d-6 DMSO, δ): 1.08 (3H, d, J=7 Hz), 2.7-3.3 (3H), 3.70 (3H, s), 3.6-4.3 (5H), 6.6-8.4 (10H).

(ii) (2S,1'R)-isomer of formula (11); Yield: 66.4%

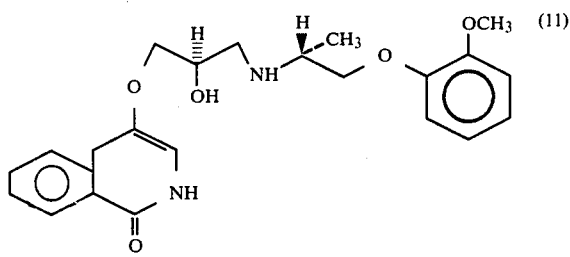

M.P. 108.3°–113.1° C.

$[\alpha]_D^{20} = -12.3°$ (c=1, CHCl$_3$—MeOH(4:1)).

NMR(CDCl$_3$, δ): 1.15 (3H, d, J=7 Hz), 2.7–3.4 (3H), 3.76 (3H, s), 3.6–4.3 (5H), 6.6–8.4 (10H).

(iii) (2R,1'R)-isomer of formula (12); Yield: 77.3%

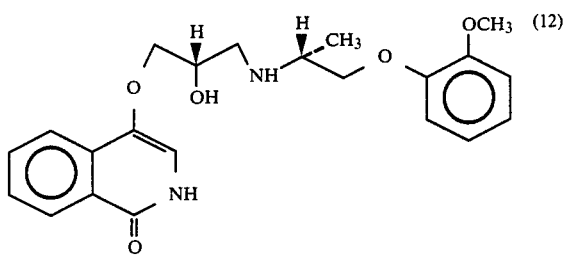

M.P. 153.2°–155.3° C.

$[\alpha]_D^{20} = -3.24°$ (c=1, CHCl$_3$—MeOH(4:1)).

NMR(d-6 DMSO, δ): 1.08 (3H, d, J=7 Hz), 2.7–3.3 (3H), 3.70 (3H, s), 3.6–4.3 (5H), 6.6–8.4 (10H).

EXAMPLE 9

A mixture of D-alanine (5.0 g) and phthalic anhydride (8.3 g) was heated at 170° C. for 2 hours. The reaction product was crystallized from 80% aqueous ethanol (water containing 80% by volume of ethanol) to afford D-phthaloylalanine (9.5 g).

A solution of D-phthaloylalanine (9.5 g) in tetrahydrofuran (50 ml) was added dropwise, under ice-water cooling and stirring, to solution in tetrahydrofuran (50 ml) of diborane which was freshly prepared by reacting sodium borohydride (1.64 g) with boron trifluoride-etherate (8.1 ml). The stirring was continued for an additional 2 hours at room temperature, after which the resulting reaction solution is poured into a dilute hydrochloric acid, followed by extraction ethyl acetate. The extracted phase was separated and washed with an aqueous sodium carbonate solution, dried and then distilled to remove the ethyl acetate. The residue was chromatographed on a silica gel column with benzene-ethyl acetate as eluent, yielding (R)-N-(2-hydroxy-1-methylethyl)-phthalimide (6.22 g; 69.9%).

$[\alpha]_D^{20} = -13.76°$ (c=1, CHCl$_3$).

NMR(CDCl$_3$, δ): 1.42 (3H, d, J=7 Hz), 3.2 (1H, disappeared in D$_2$O), 3.7–4.6 (3H), 7.6–7.9 (4H).

EXAMPLE 10

A mixture of (L)-2-aminopropanol (20 g) and phthalic anhydride (39.5 g) was heated at 170° C. for 1 hour. The crude product obtained was chromatographed on a silica gel column with benzene-ethyl acetate as eluent, giving (S)-N-(2-hydroxy-1-methylethyl)-phthalimide (46.5 g; 85%).

$[\alpha]_D^{20} = +16.47°$ (c=1, CHCl$_3$).

EXAMPLE 11

A mixture of (S)-N-(2-hydroxy-1-methylethyl)-phthalimide (46.5 g) and p-toluenesulfonyl chloride (43.9 g) in pyridine was stirred at room temperature overnight.

The resulting reaction solution was poured into water, followed by extraction with ethyl acetate. The extract was washed with a dilute hydrochloric acid, dried and distilled to remove the ethyl acetate. Recrystallization of the resulting residue from ethyl acetate gave (S)-N-(2-tosyloxy-1-methylethyl)-phthalimide 2.4 g; 88.9%) as white crystals.

$[\alpha]_D^{22} = +19.93°$ (c=1, CHCl$_3$).

NMR(CDCl$_3$, δ): 1.41 (3H, d, J=7 Hz), 2.37 (3H, s), 4.1–4.7 (3H), 7.0–7.85 (8H).

EXAMPLE 12

Following the procedure of Example 11, (R)-N-(2-tosyloxy-1-methylethyl)-phthalimide (29.8 g; 85.2%) was obtained from (R)-N-(2-hydroxy-1-methylethyl)-phthalimide (20.0 g).

$[\alpha]_D^{20} = -18.81°$ (c=1, CHCl$_3$).

EXAMPLE 13

Guaiacol (9.3 cc) was added dropwise at room temperature to a solution of sodium hydride (60% Nujol, 3.0 g) in dimethylformamide (100 ml), to which was then added (R)-N-(2-tosyloxy-1-methylethyl)-phthalimide (12.0 g), and the resulting mixture was heated at 90° C. for 4 hours.

The resulting reaction solution was poured into water, followed by extraction with ether. The ethereal layer was separated and washed with a 10% aqueous sodium hydroxide solution, dried and then distilled to remove the ether. The residue was chromatographed on a silica gel column with benzene-ethyl acetate as eluent, yielding (R)-N-(2-(o-methoxyphenoxy)-1-methylethyl)-phthalimide (4.2 g; 40.4%).

NMR(CDCl$_3$, δ): 1.52 (3H, d, J=7 Hz), 3.60 (3H, s), 4.1–5.0 (3H), 6.7–7.0 (4H) 7.5–7.95 (4H).

This product (4.2 g) was dissolved in ethanol (50 cc) and hydrazine hydrate (6 ml) was added to the resulting solution, and the mixture obtained was heated under reflux for 2 hours. The reaction solution was then extracted with chloroform and the extract was washed with a 10% aqueous sodium hydroxide solution, dried and then distilled to remove the chloroform, resulting (R)-2-(o-methoxyphenoxy)-1-methylethylamine (2.4 g; 98.1%).

$[\alpha]_D^{20} = -19.34°$ (c=1, CHCl$_3$)

NMR(CDCl$_3$, δ): 1.07 (3H, d, J=7 Hz), 1.50 (2H, s, disappeared in D$_2$O), 3.0–4.0 (6H; 3.74, OCH$_3$), 6.82 (4H, s).

EXAMPLE 14

Following the procedure of Example 13, (S)-2-(o-methoxyphenoxy)-1-methylethylamine (Yield 29%) is obtained from (S)-N-(2-tosyloxy-1-methylethyl)-phthalimide.

$[\alpha]_D^{20} = +20.96°$ (c=1, CHCl$_3$).

NMR(CDCl$_3$, δ): 1.07 (3H, d, J=7 Hz), 1.49 (2H, s, disappeared in D$_2$O), 3.0–4.0 (6H; 3.74, OCH$_3$), 6.82 (4H, s).

What we claim is:

1. An optically active isocarbostyril derivative isolated as the (S-S)-isomer, (S-R)-isomer, (R-S)-isomer or (R-R)-isomer and represented by the formula (II):

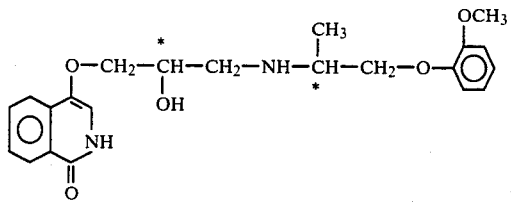
(II)

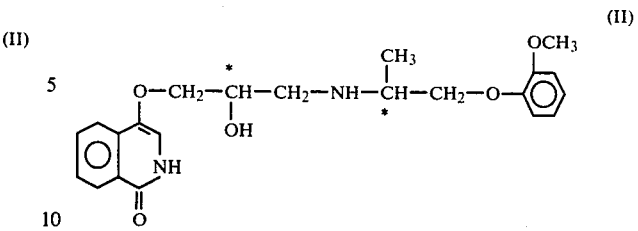
(II)

wherein the asymmetric carbon atoms, each having an asterisk attached thereto as shown, exhibit either the (S)-configuration or the (R)-configuration, or a pharmaceutically acceptable acid addition salt of said isocarbostyril derivative.

2. The compound of claim 1 which is selected from the group consisting of:

(2R,1′S)-1-[2′-(o-methoxyphenoxy)-1′-methylethylamino]-3-(4″-isocarbostyriloxy)-2-propanol;

(2S,1′S)-1-[2′-(o-methoxyphenoxy)-1′-methylethylamino]-3-(4″-isocarbostyriloxy)-2-propanol;

(2S,1′R)-1-[2′-(o-methoxyphenoxy)-1′-methylethylamino]-3-(4″-isocarbostyriloxy)-2-propanol; and (2R,1′R)-1-[2′-(o-methoxyphenoxy)-1′-methylethylamino]-3-(4″-isocarbostyriloxy)-2-propanol.

3. A compound selected from the group consisting of (5R,1′S)-N-[2′-(o-methoxyphenoxy)-1′-methylethyl]-5-(4″-isocarbostyriloxymethyl)-2-oxazolidone; (5S,1′S)-N-[2′-(o-methoxyphenoxy)-1′-methylethyl]-5-(4″-isocarbostyriloxymethyl)-2-oxazolidone; (5S,1′R)-N-[2′-(o-methoxyphenoxy)-1′-methylethyl]-5-(4″-isocarbostyriloxymethyl)-2-oxazolidone; and (5R,1′R)-N-[2′-(o-methoxyphenoxy)-1′-methylethyl]-5-(4″-isocarbostyriloxymethyl)-2-oxazolidone.

4. A process of isolating the four optically active isomers, namely, the (2R,1′S)-isomer, (2S,1′S)-isomer, (2S,1′R)-isomer and (2R,1′R)-isomer of 1-[2′-(o-methoxyphenoxy)-1′-methylethylamino]-3-(4″-isocarbostyryloxy)-2-propanol represented by the formula (II):

wherein the asymmetric carbon atoms each having the asterisk attached thereto as shown exhibit either the (S)-configuration or the (R)-configuration in each isomer, which comprises (a) chromatographically separating, by means of liquid chromatography on a silanized silica gel substrate, a diastereomeric mixture of compounds of formula I

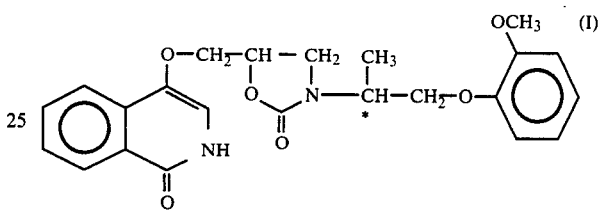
(I)

wherein the asterisked asymmetric carbon atom has the (R)-configuration and the non-asterisked asymmetric carbon atom has the (R)- or (S)-configuration, into its optical antipodes, (b) chromatographically separating, by means of a liquid chromatography on a silanized silica gel substrate, a compound of formula I wherein the asterisked asymmetric carbon atom has the (S)-configuration and the non-asterisked asymmetric carbon atom has the (R)- or (S)-configuration, into its optical antipodes, to separately isolate the respective four optical isomers, namely, (5R,1′S)-N-[2′-(o-methoxyphenoxy)-1′-methylethyl]-5-(4″-isocarbostyryloxymethyl)-2-oxazolidone, (5S,1′S)-N-[2′-(o-methoxyphenoxy)-1′-methylethyl]-5-(4″-isocarbostyryloxymethyl)-2-oxazolidone, (5S,1′R)-N-(2′-(o-methoxyphenoxy)-1′methylethyl]-5-(4″-isocarbostyryloxymethyl)-2-oxazolidone and (5R,1′R)-N-[2′-(o-methoxyphenoxy)-1′-methylethyl]-5-(4″-isocarbostyryloxymethyl)-2-oxazolidone, and, (c) hydrolyzing each of these four optical isomers separately to produce the (2R,1′S)-isomer, the (2R,1′R)-isomer, the (2S-1′S)-isomer and the (2S-1′R)-isomer, respectively, of 1-[2′-(o-methoxyphenoxy)-1′-methylethylamino]-3-(4″-isocarbostyryloxy)-2-propanol of the formula (II), above.

* * * * *